United States Patent [19]

Weaver et al.

[11] Patent Number: 4,749,774

[45] Date of Patent: Jun. 7, 1988

[54] CONDENSATION POLYMER CONTAINING THE RESIDUE OF A POLY-METHINE COMPOUND AND SHAPED ARTICLES PRODUCED THEREFROM

[75] Inventors: Max A. Weaver; Clarence A. Coates, Jr.; Wayne P. Pruett, all of Kingsport; Samuel D. Hilbert, Jonesborough, all of Tenn.

[73] Assignee: Eastman Kodak Company, Rochester, N.Y.

[21] Appl. No.: 78,434

[22] Filed: Jul. 27, 1987

Related U.S. Application Data

[63] Continuation-in-part of Ser. No. 947,136, Dec. 29, 1986.

[51] Int. Cl.$^4$ .................. C08G 63/44; C08G 63/76; C08G 69/44
[52] U.S. Cl. .................................. 528/288; 525/46; 525/445; 528/183; 528/192; 528/193; 528/194; 528/289; 528/290; 528/302; 528/304
[58] Field of Search .............. 528/288, 289, 290, 302, 528/304, 183, 192–194; 525/445, 46

[56] References Cited

U.S. PATENT DOCUMENTS

| | | | |
|---|---|---|---|
| 3,597,434 | 8/1971 | Weaver | 546/165 |
| 4,297,502 | 10/1981 | Herrmann et al. | 528/288 X |
| 4,338,247 | 7/1982 | Zannucci et al. | 528/307 |
| 4,617,373 | 10/1986 | Pruett et al. | 528/288 |

Primary Examiner—Lucille M. Phynes
Attorney, Agent, or Firm—J. Frederick Thomsen; William P. Heath, Jr.

[57] ABSTRACT

Composition useful for molding into articles which as food containers, beverage bottles, cured structural plastics and the like comprising molding grade linear or unsaturated polyester or polycarbonate having reacted therewith or copolymerized therein the residue of one or more poly-methine compounds having the formula:

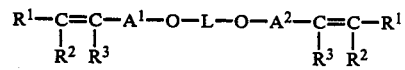

wherein each $R^1$ is independently selected from cyano, carboxy, alkenyloxycarbonyl, or a substituted or unsubstituted alkoxycarbonyl, cycloalkoxycarbonyl or aryloxycarbonyl radical;

each $R^2$ is independently selected from one of the groups specified for $R^1$ or an unsubstituted or substituted aryl, carbamoyl, alkanoyl, cycloalkanoyl, aroyl, alkylsulfonyl, cycloalkylsulfonyl, arylsulfonyl or aromatic, heterocyclic radical;

each $R^3$ is independently selected from hydrogen or an unsubstituted or substituted alkyl, cycloalkyl or aryl radical;

$A^1$ and $A^2$ are independently selected from 1,4-phenylene radicals; and

L is an organic linking group bonded by non-oxo carbon atoms to the oxygen atoms adjacent to L; provided the poly-methine compound bears at least one substituent that is reactive with one of the monomers from which the condensation polymer is derived.

The polymethine residues are present in the polymer as an integral part of the polymer chain and absorb ultraviolet radiation in the range of about 250 to about 390 nm. The residues are non-extractable from the polymer and stable at the conditions at which the polymers are manufactured and processed.

28 Claims, No Drawings

CONDENSATION POLYMER CONTAINING THE RESIDUE OF A POLY-METHINE COMPOUND AND SHAPED ARTICLES PRODUCED THEREFROM

This application is a continuation-in-part of our co-pending Application Ser. No. 947,136, filed Dec. 29, 1986, for "Condensation Copolymers Containing Bis-Methine Moieties and Products Therefrom".

DESCRIPTION

This invention pertains to novel condensation polymers such as polyesters and polycarbonates wherein one or more poly-methine moieties have been incorporated in the chain or backbone of the polymer. This invention also pertains to fibers and, particularly, to containers, such as those suitable for packaging beverages and foods, manufactured from our novel condensation polymers.

Many products such as certain fruit juices, soft drinks, wines, food products, cosmetics and shampoos are deleteriously affected, i.e., degraded, by ultraviolet (UV) light when packaged in clear plastic containers which pass significant portions of the available light at wavelengths in the range of approximately 250 to 390 nm. It is well known the polymers can be rendered resistant to degradation by UV light by physically blending in such polymers various UV light stabilizers such as benzophenones, benzotriazoles and resorcinol monobenzoates. See, for example, Plastics Additives Handbook, Hanser Publishers, Library of Congress, Catalog No. 83-062289, pp 128-134. Normally, such stabilizers are used in a weight concentration of at least 0.5 percent. Although these stabilizers generally function well to absorb radiation in the range of about 300 to 350 nm, absorbence in the range of 300 to 350 nm is not adequate to protect comestibles subject to UV light degradation packaged in clear plastic, i.e., essentially colorless, transparent plastics. The stabilizers present in many of the known stabilized polymer compositions can be extracted from the polymer by solvents such as acids, alcohols and the like present in foods or beverages packaged within the stabilized polymers. Furthermore, many compounds used to stabilize polymers are not stable at high temperatures and decompose under the conditions at which polyesters are manufactured or processed. Decomposition of such stabilizers frequently causes yellow discoloration of the polymer and results in the polymer containing little, if any, of the stabilizer.

U.S. Pat. No. 3,634,320 discloses certain bis-methine compounds and their use as UV absorbers in various addition and condensation polymers. The patent does not specify that the bis-methine compounds react or copolymerize with any of the condensation polymers disclosed. The bis-methine compounds were intended for use as stabilizers in concentrations in the polymer of up to 5%, preferably in the range of 0.1 to 0.2%.

U.S. Pat. Nos. 4,305,719, 4,338,247, 4,430,718 and 4,617,374 disclosed the concept of reacting benzylidene-type methine compounds capable of absorbing UV light with or into polyesters. These patents do not, however, disclose the use of the methine compounds described hereinafter to obtain the compositions provided by this invention.

The novel polymer composition provided by our invention comprises molding or fiber grade condensation polymer having copolymerized therein or reacted therewith the residue of a poly-methine compound or mixture of poly-methine compounds having the formula:

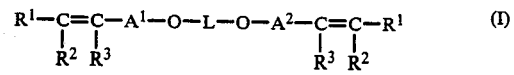

wherein each $R^1$ is independently selected from cyano, carboxy, alkenyloxycarbonyl, or a substituted or unsubstituted alkoxycarbonyl, cycloalkoxycarbonyl or aryloxycarbonyl radical;

each $R^2$ is independently selected from one of the groups specified for $R^1$ or an unsubstituted or substituted aryl, carbamoyl, alkanoyl, cycloalkanoyl, aroyl, alkylsulfonyl, cycloalkylsulfonyl, arylsulfonyl or aromatic, heterocyclic radical;

each $R^3$ is independently selected from hydrogen or an unsubstituted or substituted alkyl, cycloalkyl or aryl radical;

$A^1$ and $A^2$ are independently selected from 1,4-phenylene radicals; and

L is an organic linking group bonding by non-oxo carbon atoms to the oxygen atoms adjacent to L; provided the poly-methine compound bears at least one substituent that is reactive with one of the monomers from which the condensation polymer is derived, said poly-methine residue absorbing radiation in the range of about 250 nm to about 390 nm, and being non-extractable from said polymer and stable under the polymer processing conditions.

The alkyl and alkoxy moieties of the groups recited in the definitions of $R^1$, $R^2$, and $R^3$ can be unsubstituted or substituted alkyl and alkoxy of up to about 12 carbon atoms. Hydroxy, alkoxy, halogen, alkanoyloxy, alkoxycarbonyl, cyano, aryl, aryloxy, cycloalkyl, cycloalkoxy and alkylthio are examples of the substituents which may be present on the substituted alkyl groups and alkoxy moieties which $R^1$, $R^2$, and $R^3$ can represent. The cycloalkyl moieties of the groups recited in the definitions of $R^1$, $R^2$, and $R^3$ can be unsubstituted cycloalkyl of 5 to 7 carbon atoms which may be substituted with alkyl or any of the substituents mentioned hereinabove. The carbamoyl groups which $R^2$ can represent may be unsubstituted or substituted carbamoyl such as N-alkylcarbamoyl, N,N-dialkylcarbamoyl, N-cycoalkylcarbamoyl, N-alkyl-N-cycloalkylcarbamoyl, N-arylcarbamoyl, N-alkyl-N-arylcarbamoyl and the like.

The aryl moieties of the groups recited in the definitions of $R^1$, $R^2$, and $R^3$ can be unsubstituted or substituted carbocyclic aryl containing 6 to about 12 carbon atoms. Examples of the substituents which may be present on the aryl groups include alkyl and the substituents set forth in the preceding paragraph. Pyrolyl, pyridyl, pyrimidyl, 2-benzothiazolyl, 2-benzoxazolyl, 2-benzimidazolyl, 2-thienyl, 2-furanyl, 1,3,4-thiadiazol-2-yl, 1,2,4-thiadiazol-2-yl and groups having the structure:

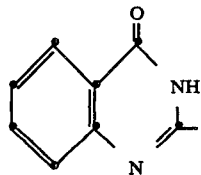

are examples of the unsubstituted aromatic heterocyclic residues which each $R^2$ may represent.

The 1,4-phenylene residues can be unsubstituted or substituted, for example, with alkyl, alkoxy, halogen, hydroxy, alkoxycarbonyl, etc.

Further descriptions and examples of the

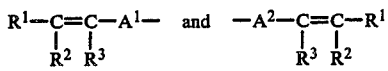

residues of the poly-methine compounds of formula (I) are set forth in U.S. Pat. Nos. 4,338,247, 4,340,718, 4,617,374 and 4,661,566, the disclosures of which are incorporated herein by reference.

The organic linking represented by L is bonded to the adjacent oxygen atoms through non-oxo carbon atoms, e.g., unsubstituted or substituted methylene groups, a methylidene group and an unsubstituted methylene group or a nuclear carbon atom of a carbocyclic or heterocyclic aromatic group. Thus, linking group L is selected from a wide variety of alkylene, alkenylene, alkynylene, cycloalkylene, carbocyclic and heterocyclic arylene and combinations of such divalent groups. The alkylene linking groups may contain within their main chain hetero atoms, e.g., oxygen, sulfur, sulfonyl, nitrogen, substituted nitrogen, and/or cyclic groups such as cycloalkylene, carbocyclic arylene, or divalent aromatic heterocyclic groups. Examples of alkylene linking groups containing a cyclic moiety in the linking chain include:

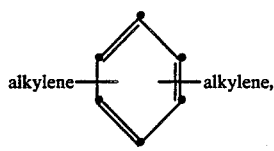

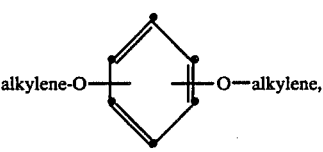

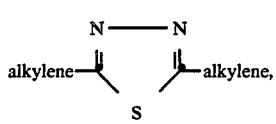

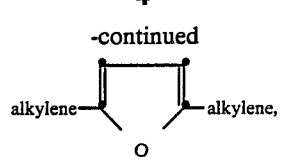

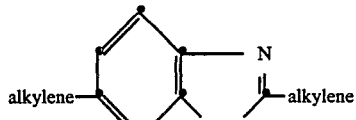

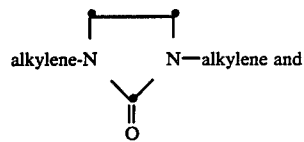

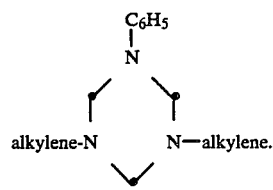

The carbocyclic arylene groups may be cycloalkylene such as 1,2-, 1,3- and 1,4-cyclohexylene, 1,2-, 1,3- and 1,4-phenylene and 2,6- and 2,7-naphthylene. Examples of the divalent heterocyclic groups include unsubstituted and substituted triazines such as 1,3,5-triazin-2,4-diyl, 6-methoxy-1,3,5-triazin-2,4-diyl and the group having the structure:

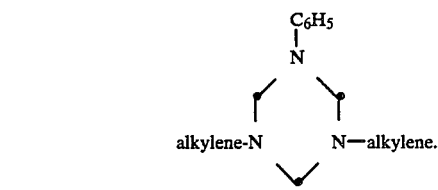

diazines such as 2,4-pyrimidindiyl, 6-methyl-2,4-pyrimidindiyl, 6-phenyl-2,4-pyrimidindiyl, 3,6-pyridazindiyl and 2-methyl-3-oxo-4,5-pyridazindiyl; dicyanopyridines such as 3,5-dicyano-2,6-pyridindiyl and 4-phenyl-3,5-cyano-2,6-pyridindiyl; quinolines and isoquinolines such as 2,4-quinolindiyl and 2,8-isoquinolinediyl; quinoxalines such as 2,3-quinoxalindiyl; and azoles such as 2,5-thiazoldiyl, 5-methylene-2-thiazolyl, 3,5-isothiazoldiyl, 5-methylene-3-isothiazolyl, 1,3,4-thiadiazol-2,5-diyl, 1,2,4-thiadiazol-3,5-diyl, 2,6-benzothiazoldiyl, 2,5-benzoxazoldiyl, 2,6-benzimidazoldiyl, 6-methylene-2-benzothiazolyl and the group having the structure:

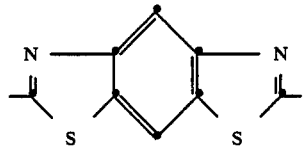

and maleimides such as 1-methyl-3,4-maleimidediyl and 1-phenyl-3,4-maleimidediyl. The acyclic moieties of the linking group represented by L also may be substituted, for example, with hydroxy, alkoxy, halogen, alkanoyloxy, cyano, alkoxycarbonyl, aryl, aryloxy, cycloalkyl, etc. The cyclic moieties of linking group L may be substituted with alkyl as well as with the substituents already mentioned. In addition to the possible substitution described above, the nitrogen atom of the nitrogen containing alkylene groups may be substituted, for example, with alkyl, aryl, alkanoyl, aroyl, alkylsulfonyl, or carbamoyl, e.g.,

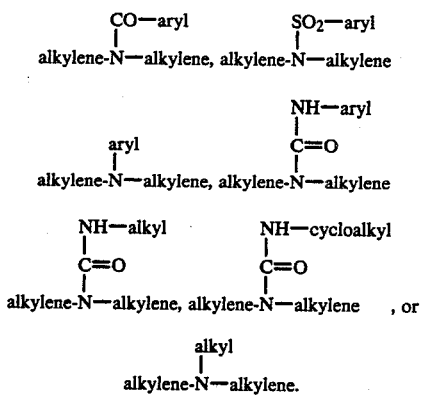

As stated hereinabove, the poly-methine compounds must bear or contain at least one substituent that is reactive with one of the monomers from which the condensation polymer is derived. Examples of such reactive substituents include carbonyl halides such as carbonyl chloride, carboxy, alkoxycarbonyl, alkenyloxycarbonyl, cycloalkoxycarbonyl, aryloxycarbonyl, amino, hydroxy, esterified hydroxy, i.e., acyloxy, groups such as carboxylic acid esters, e.g., alkanoyloxy, cycloalkanoyloxy and aroyloxy, carbamic acid esters, esters, e.g., N-alkylcarbamoyloxy and N-arylcarbamoyloxy and carbonate esters, e.g., ethoxycarbonyloxy. The poly-methine residue may be incorporated into or on the polymer chain by reacting one or more poly-methine compounds of formula (I) with the monomers, with a prepolymer or with the final polymer. As those skilled in the art will appreciate, when the reactive substituent or substituents are alkoxycarbonyl, alkenyloxycarbonyl, cycloalkoxycarbonyl, aryloxycarbonyl, or acyloxy, the alkyl, alkenyl, cycloalkyl and aryl residues and the acid residues of the acyloxy substituents are displaced or removed from the poly-methine compound upon reaction with the polymer or polymer precursor. Thus, those residues are not important to the polymethine residue component of our novel compositions.

In one embodiment of our invention, the polymethine residue is derived from a bis-methine compound having the formula:

$$R^4OCC=C-A-O-L-O-A-C=CCOR^4 \quad (II)$$
$$\overset{\|}{O} \quad \overset{|}{R^2} \overset{|}{R^3} \quad \quad \overset{|}{R^3} \overset{|}{R^2} \quad \overset{\|}{O}$$

wherein
$R^4$ is hydrogen, alkyl, cycloakyl or aryl;
each $R^2$ is cyano, aryl, acyl, especially alkanoyl, aromatic heterocyclic, alkylsulfonyl, arylsulfonyl,
aroyl, carbamoyl or carbamoyl substituted with aryl, alkyl or cycloalkyl;
each $R^3$ is hydrogen, alkyl, aryl, or cycloalkyl;
A is 1,4-phenylene; and
L is alkylene, alkylene—O—alkylene, alkylene—SO$_2$—alkylene, alkylene—S—alkylene,

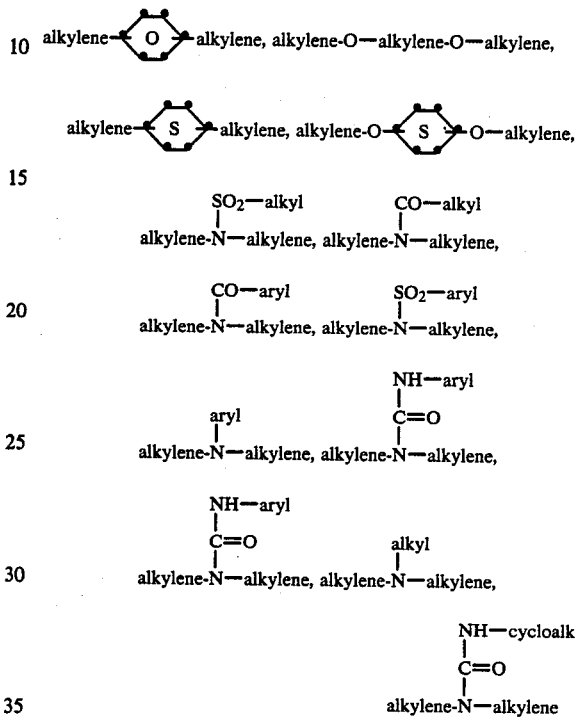

arylene, or cyclohexylene; wherein each alkyl, alkylene, aryl, arylene, cycloalkyl or cycloalkylene moiety or portion of a group or radical may be substituted where appropriate with 1-3 of hydroxyl, acyloxy, alkyl, cyano, alkoxycarbonyl, halogen, alkoxy, aryl, aryloxy, or cycloalkyl; wherein in all of the above definitions the alkyl or alkylene moieties or portions of the various groups contain from 1-8 carbons, straight or branched chain, the aryl or arylene nuclei contain from 6-10 carbons, and the cycloalkyl or cycloalkylene nuclei contain from 5-6 carbons.

In the bis-methine compounds of formula (II), L preferably is ethylene, 1,4-butanediyl, 2-methyl-1,3-propanediyl, oxy-bis-ethylene, i.e., CH$_2$CH$_2$OCH$_2$CH$_2$—, sulfonyl-bis-ethylene, thio-bis-ethylene, 1,4-phenylene-bis-methylene, 1,4-cyclohexylene-bis-methylene, 1,4-phenylenebis(oxyethylene), i.e., —CH$_2$CH$_2$O—C$_6$H$_4$—OCH$_2$CH$_2$—, methylsulfonylimino-bis-ethylene, phenylimino-bis-ethylene, acetylimino-bis-ethylene, phenylsulfonylimino-bis-ethylene, 1,2-, 1,3- or 1,4-phenylene, 1,4-cyclohexylene, 1,4-phenylene-bis-ethylene, oxy-bis-1,4-butanediyl or phenylcarbamoylimino-bis-ethylene, i.e., CH$_2$CH$_2$N—(C$_6$H$_5$NHCO)—CH$_2$CH$_2$—. The bis-methine compounds which are particularly preferred has the formula:

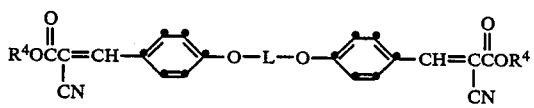

wherein R[4] is lower alkyl, i.e., alkyl containing up to about 4 carbon atoms, and L is alkylene of 2 to about 6 carbon atoms or phenylenedialkylene in which each alkylene moiety contains up to about 4 carbon atoms.

In another embodiment of our invention, organic linking group L is an alkenylene, alkynylene or substituted alkylene group such as, for example, alkylene substituted with hydroxy, carboxy, chlorocarbonyl, alkoxycarbonyl, cycloalkoxycarbonyl, aryloxycarbonyl, alkenyloxycarbonyl, carbamoyloxy wherein the carbamoyl moiety is as defined hereinabove, amino, alkylamino, alkanoyloxy, halogen, a group having the structure:

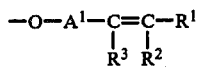

wherein R[1], R[2], R[3] and A[1] are defined hereinabove or a group having the structure —X—alkylene—R[5], —X—arylene—R[5], —X—alkylene—arylene—R[5] wherein alkylene and arylene are defined hereinabove, X is —O—, —S—, —SO—, —SO$_2$—,

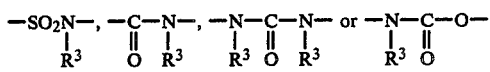

in which R[3] is defined hereinabove, and R[5] is hydrogen, hydroxy, carboxy, chlorocarbonyl, alkoxycarbonyl, cycloalkoxycarbonyl, aryloxycarbonyl, alkenyloxycarbonyl, carbamoyloxy wherein the carbamoyl moiety is as defined hereinabove, amino, alkylamino, alkanoyloxy or halogen.

The poly-methine compounds of formula (I) can be prepared using known procedures by reacting an intermediate carbonyl compound (III) with an active methylene compound (IV) under Knovenagel reaction conditions, e.g.,

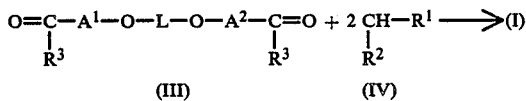

The carbonyl compounds of formula (IV) may be obtained by reacting dihalo compounds (V) with p-hydroxyphenylcarbonyl compounds (VI) according to methods known for the synthesis of ethers.

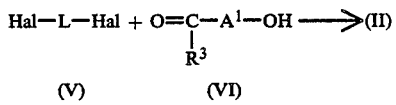

Suitable procedures are described in the chemical literature (W. J. P. Neish, Rec. trav. chim. 66, 433–42 (1947) [C.A. 42: 894a]; Hugh B. Donahoe, et. al., J. Org. Chem. 26, 474–6 (1961) [C.A. 55: 17565d]; R. Jaunin, et al., Helv. Chim Acta. 42, 328–34 (1959). The poly-methine compounds in which L is a substituted alkylene group can be obtained by first reacting a p-hydroxyphenylcarbonyl compound with a dihaloalkanol such as 1,3-dichloro-2-propanol, 2,3-dibromopropanol or 1,4-dibromo-2-butanol to obtain compounds of formula (II) wherein L is a hydroxyalkylene group. The hydroxy group present on the organic linking group L can be reacted with a variety of compounds to produce various substituents, e.g., chlorides, ethers and various types of esters.

The polyesters which may be used in the preparation of the compositions of our invention include linear, thermoplastic, crystalline or amorphous polyesters produced by conventional polymerization techniques from one or more diols and one or more dicarboxylic acids. The polyesters normally are molding or fiber grade and have an inherent viscosity (IV) of about 0.4 to about 1.2. The preferred polyesters comprise at least about 50 mole percent terephthalic acid residues and at least about 50 mole percent ethylene glycol and/or 1,4-cyclohexanedimethanol residues. Particularly preferred polyesters are those containing from about 75 to 100 mole percent terephthalic acid residues and from about 75 to 100 mole percent ethylene glycol residues.

The unsaturated, curable polyesters which may be used in our novel compositions are the polyesterification products of one or more glycols and one or more unsaturated dicarboxylic acids or their anhydrides. Typical of the unsaturated polyesters is the polyesterification product of (a) 1,4-cyclohexanedimethanol and/or 2,2-dimethyl-1,3-propanediol and optionally an additional dihydric alcohol, such as ethylene glycol, and (b) maleic acid or fumaric acid and an aromatic dicarboxylic acid, which when crosslinked with an ethylenically-unsaturated monomer, e.g., styrene, produces a cured polyester resin which has, for example, high thermal resistance, high heat distortion values, excellent electrical and mechanical properties, and excellent resistance to chemicals.

Solutions of such unsaturated polyester resins in an ethylenically-unsaturated monomer such as styrene commonly are referred to as polyester resins.

The unsaturated polyester resins may be prepared in the presence of gelation inhibitors such as hydroquinone or the like, which are well known in the art of polyesterification. The esterification may be carried out, for example, under an inert blanket of gas such as nitrogen in a temperature range of 118°-220° C. for a period of about 6–20 hours until an acid number below 100 and preferably below 50 is obtained, based on milliequivalents of KOH necessary to neutralize 1 gram of the unsaturated polyester. The resulting polyester may be subsequently copolymerized, cross-linked, or cured with "curing amounts" of any of the well-known ethylenically unsaturated monomers used as solvents for the polyester. Examples of such monomers include styrene, alpha-methyl styrene, vinyl toluene, divinyl benzene, chlorostyrene, and the like as well as mixtures thereof. Typically, the mole ratio of such unsaturated monomer to the unsaturated moiety (e.g., maleic acid residue) in the polyester is from about 0.5 to about 3.0, although the "curing amounts" of such monomer can be varied from these ratios.

It is preferred that the unsaturated polyester be prepared from one or more dihydric alcohols, fumaric or maleic acid or mixtures thereof, and up to about 60 mole percent of total acid component of o-phthalic, isophthalic or terephthalic acids or mixtures thereof. Preferred for the dihydric alcohol component is one or a mixture of propylene glycol, neopentyl glycol, 2,2,4-trimethyl-1,3-pentanediol, ethylene glycol, or diethylene glycol. A specific preferred unsaturated polyester is prepared from about 75 to 100 mole percent propylene glycol, and as the acid component, from, about 75 to 100 mole percent o-phthalic and maleic acids in a mole ratio of from about 1/2 to 2/1. Typical of these unsaturated polyesters are those disclosed, for example, in U.S. Pat. No. 4,359,570 incorporated herein by reference.

The diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

Typical polycarbonates useful herein are disclosed in Kirk-Othmer Encyclopedia of Chemical Technology, third edition, Volume 18, pages 479–494, incorporated herein by reference.

The novel polymer compositions provided by this invention are useful in the manufacture of containers or packages for comestibles such as beverages and food. By use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

The linear polyesters most preferred for use in articles having "hot-fill" stability comprise poly(ethylene terephthalate), poly(ethylene terephthalate) wherein up to 5 mole percent of the ethylene glycol residues have been replaced with residues derived from 1,4-cyclohexanedimethanol and poly(ethylene 2,6-naphthalenedicarboxylate), wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at the temperature. For the manufacture of blow-molded beverage bottles, the most preferred polyesters have an I.V. of 0.65 to 0.85, and a Tg of >70° C., and film sections cut from the bottle have a Water Vapor Transmission Rate of 1.5 to 2.5 g mils/100 in.$^2$-24 hours, a Carbon Dioxide Permeability of 20–30 cc. mils/100 in.$^2$-24 hours-atm., and an Oxygen Permeabilty of 4–8 cc. mils/100 in.$^2$-24 hours-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk River, Minn., and the Carbon Dioxide Permeability by the standard operating procedure of a MOCON PERMATRAN C II, also of Modern Controls.

The concentration of the residue of the polymethine compound in the condensation polymer can be varied substantially depending, for example, on the intended function of the UV-absorbing residue and/or the end use for which the polymer composition is intended. When the polymer composition is to be used in the fabrication of relatively thin-walled containers to screen IV light in the range of about 250 to 390 nm, the concentration of the residue of the poly-methine compound normally will be in the range of about 50 to 1500 ppm (parts by weight per million parts by weight polymer with the range of about 200 to 800 ppm being especially preferred.

When the levels of the present ultra-violet light absorbers are increased to higher levels such as 5,000 ppm (0.5 weight percent) or higher, polymers containing these ultra-violet light absorbers show improved resistance to weathering and when these polymers per se or fibers thereof are dyed with disperse dyes, at a concentration, for example, of from about 0.01 to about 5.0% based on weight of polymer or fiber, many dyes exhibit increased lightfastness. Such disperse dyes are shown, for example, in U.S. Pat. Nos. 4,305,719; 2,746,952; 2,746,953; 2,757,173; 2,763,668; 2,771,466; 2,773,054; 2,777,863; 2,785,157; 2,790,791; 2,798,081; 2,805,218; 2,822,359; 2,827,450; 2,832,761; 2,852,504; 2,857,371; 2,865,909; 2,871,231; 3,072,683; 3,079,373; 3,079,375; 3,087,773; 3,096,318; e,096,332; 3,236,843; 3,254,073; 3,349,075; 3,380,990; 3,386,990; 3,394,144; 3,804,823; 3,816,388; 3,816,392; 3,829,410; 3,917,604; 3,928,311; 3,980,626; 3,998,801; 4,039,522; 4,052,379; and 4,140,683, the disclosures of which are incorporated herein by reference.

Polymer compositions containing substantially higher amounts, e.g., from about 2.0 to 10.0 weight percent, of the residue of one or more of the polymethine compounds described herein may be used as polymer concentrates. Such concentrates may be blended with the same or different polymer according to conventional procedures to obtain polymer compositions which will contain a predetermined amount of the residue or residues in a non-extractable form. In the preparation of these highly loaded, polymer composition concentrates the residue preferably is divalent and thus is derived from a difunctional poly-methine compound such as the compound of Example 1.

The preparation of the poly-methine compound and their use in preparing the compositions of our invention are further illustrated by the following examples.

EXAMPLE 1

To absolute ethanol (50 mL) is added metallic sodium (1.5 g, 0.05 m) in small pieces and stirring continued to complete solution. p-Hydroxybenzaldehyde (6.1 g, 0.05 m) is added, followd by 1,2-dibromoethane (4.6 g, 0.025 m). The reaction mixture is heated at reflux for six hours and then cooled to precipitate the product, 4,4'-ethylenedioxydibenzaledehyde. The product is collected by filtration, washed with ethanol, and dried. M.P. 119°–121° C. 4,4'-Ethylenedioxydibenzaldehyde (1.0 g, 0.0037 m), methyl cyanoacetate (0.74 g, 0.0074 m), methanol (30 mL), and two drops of piperidine are heated at reflux for one hour and allowed to cool. The product is collected by filtration, washed with methanol, and dried in air (yield—1.4 g). The product, dimethyl 3,3′-[1,2-ethanediyl-bis(oxy-1,4-phenylene)]-bis-[2-cyano-2-propenoate], has an absorption maximum at 366 nm in acetone and an extinction coefficient of 50,112 and has the structure:

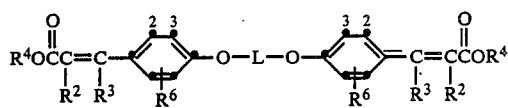

TABLE I

| Ex. | $R^4$ | $R^2$ | $R^3$ | $R^6$ | L |
|---|---|---|---|---|---|
| 2 | —CH$_3$ | —CN | H | 3-OCH$_3$ | —CH$_2$CH$_2$— |
| 3 | —CH$_3$ | —CN | —CH$_3$ | H | —CH$_2$CH$_2$— |
| 4 | —CH$_3$ | —CN | —C$_6$H$_5$ | H | —(CH$_2$)$_3$— |
| 5 | —C$_2$H$_5$ | —CN | —C$_6$H$_{11}$ | H | —CH$_2$CH$_2$— |
| 6 | —CH$_2$CH$_2$OH | —CN | H | H | —CH$_2$CH$_2$OCH$_2$CH$_2$— |
| 7 | —CH$_2$CH$_2$OC$_2$H$_5$ | —CN | H | H | —CH$_2$CH$_2$SCH$_2$CH$_2$— |
| 8 | —CH$_2$CH$_2$CN | —CN | H | H | —CH$_2$CH$_2$SO$_2$CH$_2$CH$_2$— |
| 9 | —CH$_2$CH$_2$C$_6$H$_5$ | —CN | H | H | —(CH$_2$)$_4$— |
| 10 | —CH$_2$CH$_2$OC$_6$H$_5$ | —CN | H | H | —CH$_2$— |
| 11 | —C$_6$H$_{11}$ | —CN | H | H | —(CH$_2$)$_4$— |
| 12 | —CH$_2$C$_6$H$_{11}$ | —CN | H | H | —CH$_2$CH$_2$— |
| 13 | —CH$_2$C$_6$H$_5$ | —CN | H | H | —CH$_2$CH$_2$OCH$_2$CH$_2$— |
| 14 | —C$_6$H$_5$ | —CN | H | H | —CH$_2$CH$_2$— |
| 15 | —CH$_3$ | —CN | H | H | —(CH$_2$)$_3$— |
| 16 | —(CH$_2$)$_3$CH$_3$ | —CN | H | H | —CH$_2$CH$_2$— |
| 17 | —CH$_3$ | —CN | H | H | —CH$_2$C$_6$H$_4$—4-CH$_2$— |
| 18 | —CH$_3$ | —CN | H | H | —CH$_2$C$_6$H$_{11}$—4-CH$_2$— |
| 19 | —CH$_3$ | —CN | H | H | —CH$_2$CH$_2$OC$_6$H$_4$—4-OCH$_2$CH$_2$— |
| 20 | —CH$_3$ | —CN | H | 2-OCH$_3$ | —CH$_2$CH$_2$ |
| 21 | —CH$_3$ | —CN | H | 3-OCH$_3$ | —CH$_2$C$_6$H$_4$—4-CH$_2$— |
| 22 | —CH$_3$ | —CONH$_2$ | H | 3-OCH$_3$ | —CH$_2$CH$_2$N(SO$_2$CH$_3$)CH$_2$CH$_2$— |
| 23 | —CH$_3$ | —CONHC$_2$H$_5$ | H | 3-OCH$_3$ | —CH$_2$CH$_2$N(SO$_2$C$_6$H$_5$)CH$_2$CH$_2$— |
| 24 | —CH$_3$ | —CONHC$_6$H$_5$ | H | 3-CH$_3$ | —CH$_2$CH$_2$N(C$_6$H$_5$)CH$_2$CH$_2$— |
| 25 | —CH$_3$ | —CON(C$_2$H$_5$)$_2$ | H | 2-Cl | —CH$_2$CH$_2$N(COCH$_3$)CH$_2$CH$_2$— |
| 26 | —CH$_3$ | —C=N—1,2-C$_6$H$_4$O | H | H | —CH$_2$CH$_2$N(COC$_6$H$_{11}$)CH$_2$CH$_2$— |
| 27 | —CH$_3$ | —C=NN=CO | H | H | —CH$_2$CH$_2$C$_6$H$_4$—4CH$_2$CH$_2$— |
| 28 | —CH$_3$ | —C=N—1,2-C$_6$H$_4$S | H | H | —(CH$_2$)$_4$O(CH$_2$)$_4$— |
| 29 | —CH$_3$ | —C=NN=CS | H | H | —1,4-C$_6$H$_{10}$— |
| 30 | —CH$_3$ | —CON(CH$_3$)C$_6$H$_5$ | H | H | —1,4-C$_6$H$_4$— |
| 31 | —CH$_3$ | —SO$_2$C$_6$H$_5$ | H | H | —1,4-C$_6$H$_4$— |
| 32 | —CH$_3$ | —SO$_2$CH$_3$ | H | H | —CH$_2$CH$_2$N(CONHC$_6$H$_5$)CH$_2$CH$_2$ |
| 33 | —CH$_3$ | —COC$_6$H$_5$ | H | H | —CH$_2$CH$_2$— |
| 34 | —CH$_3$ | —COCH$_3$ | H | H | —(CH$_2$)$_3$— |
| 35 | —CH$_3$ | —C=N—1,2-C$_6$H$_4$NH | H | H | —CH$_2$CH$_2$— |
| 36 | —CH$_3$ | —C$_6$H$_4$—4-Cl | H | H | —CH$_2$CH$_2$— |

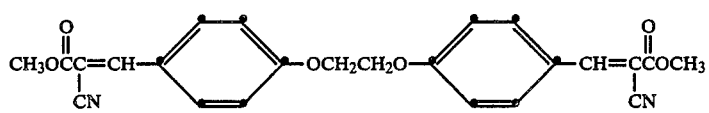

Additional examples of methine compounds which may be used in the preparation of our novel polymer compositions are set forth in Table I. These compounds may be prepared according to the procedures described above and conform to the formula:

EXAMPLE 37

Vanillin (91.2 g, 0.60 mol) is dissolved in water (500 mL) containing sodium hydroxide (24.0 g). To this solution is added 1,3-dichloro-2-propanol (38.7 g, 0.30 mol) and the reaction mixture is stirred and heated at reflux for 8 hours. Upon cooling to room temperature the product crystallizes and is collected by filtration, washed with water and dried. The crude product is recrystallized from 2 L ethanol, filtered, washed with ethanol and air dried. The purified product, 4,4′-[(2-hydroxy-1,3-propanediyl)bis(oxy)]bis[3-methoxybenzaldehyde], is obtained as a white solid in a yield of 74.3 g; 68.7% of theory. Mass spectroscopy analysis supports the structure:

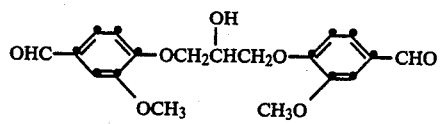

A mixture of 4,4′-[(2-hydroxy-1,3-propanediyl)bis[3-methoxy-benzaldehyde] (3.60 g, 0.01 m), ethyl cyanoacetate (2.26 g, 0.02 m), ethanol (100 mL), piperidine (10 drops), and acetic acid (5 drops) is heated at reflux for 4 hours and then allowed to cool. The essentially white product is collected by filtration, washed with ethanol, and dried in air (yield—3.5 g). Mass spectrum analysis supports the following structure:

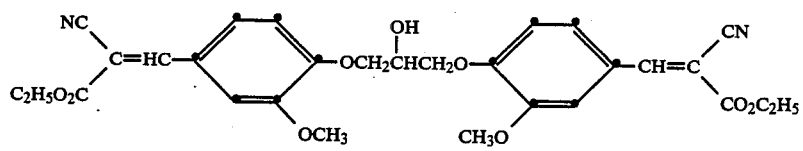

The product, diethyl 3,3′-[(2-hydroxy-1,3-propanediyl)-bis(oxy)bis(3-methoxy-4,1-phenylene)]bis[2-cyano-2-propenoate], has an absorption maximum (λmax) at 360 nm in methylene chloride.

EXAMPLE 38

Using the same procedure as described in Example 37 4,4′-[(2-hydroxyl-1,3-propanediyl)bis(oxy)]bis[3-methoxy-benzaldehyde](3.60 g, 0.01 m) is reacted with methylsulfonylacetonitrile (2.38 g, 0.02 m) using ethanol as solvent (yield—4.0 g). When dissolved in methylene chloride, the product has an absorption maximum (λmax) at 361 nm in the UV absorption spectrum. Mass spectroscopy supports the following structure:

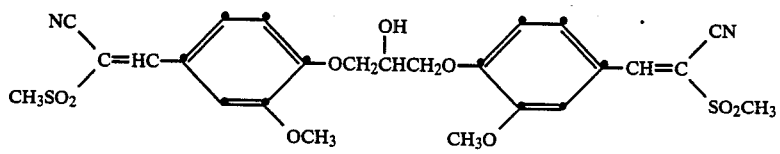

EXAMPLE 39

A mixture of 4,4′-[2-hydroxy-1,3-propanediyl)bis(oxy)]bis[3-methoxy-benzaldehyde] (3.60 g, 0.01 m), malononitrile (1.32 g, 0.02 m), and ethanol 100 mL) is heated at reflux until complete solution is obtained. Piperidine (10 drops) and acetic acid (5 drops) are added and refluxing continued for 2 hours. The pale yellow product, which crystallizes as the reaction progresses, is collected by filtration, washed with ethanol, and dried in air (yield—2.5 g). When dissolved in methylene chloride, the product has an absorption maximum (λmax) at 374 nm in the ultra-violet light absorption spectrum. The following structure is supported by mass spectroscopy analysis:

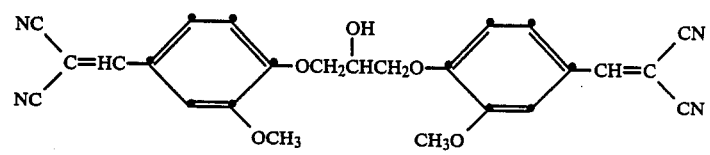

EXAMPLE 40

A mixture of p-hydroxybenzaldehyde (73.2 g, 0.60 m), 1,3-dichloro-2-propanol, water (500 mL), and sodium hydroxide (24 g) is heated at reflux for 8 hours. After beiang cooled to about 10° C., the product is collected by filtration, washed with water, and dried in air. It is placed in 300 mL of methanol and the mixture heated to boiling and allowed to cool to room temperature. After being collected by filtration, the product is washed with methanol and dried in air. There is obtained 55.9 g (62% of the theoretical yield) of essentially white product which mass spectroscopy indicates is 4,4′-[(2-hydroxy-1,3-propanediyl)bis(oxy)]bis[benzaldehyde]. A mixture of 4,4′-[(2-hydroxy-1,3-propanediyl)-bis(oxy)]bis[benzaldehyde] (300 g, 0.01 m), ethyl cyanoacetate (2.26 g, 0.02 m), N,N-dimethylformamide (10 mL), piperidine (6 drops), and acetic acid (2 drops) is heated for 2 hours at about 80° C. and then drowned into ethanol (50 mL). The almost white product is collected by filtration, washed with ethanol, and dried in air (yield—3.3 g). It has an extinction coefficient of 56,319 at 339 nm in methylene chloride. Mass spectrum analysis supports the following structure:

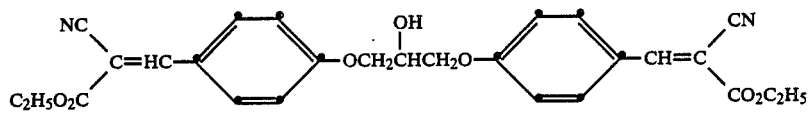

EXAMPLE 41

To water (150 mL) to which 17 g of 50% sodium hydroxide have been added, is added p-hydroxybenzaldehyde (24.4 g, 0.20 m), followed by 2,3-dibromopropanol (21.8 g, 0.10 m). The mixture is heated at reflux for 6 hours and allowed to cool which results in crystallization of the product, which is collected by filtration, washed with water, and dried in air. The yield is 23 g (76.7% of the theoretical yield) of 4,4'-[(1-(hydroxymethyl)-1,2-ethanediyl]bis(oxy)bis[benzaldehyde] as indicated by mass spectrum analysis. A mixture of the bis-aldehyde (3.0 g, 0.01 m), ethyl cyanoacetate (2.26 g, 0.02 m), N,N-dimethylformamide and 10 drops piperidine is heated for 4 hours at about 80° C. and then drowned into methanol (200 mL). The product crystallizes upon cooling to room temperature and is collected by filtration, washed with ethanol and dried in air (yield—2.1 g). The product has an absorption maximum at 339 nm in methylene chloride and has the following structure as evidenced by mass spectroscopy analysis.

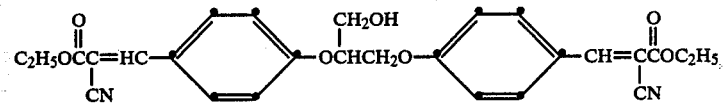

EXAMPLE 42

A mixture of p-hydroxybenzaldehyde (24.4 g, 0.40 m), 1,4-dibromo-2-butanol (23.2 g, 0.10 m), water (150 mL), and sodium hydroxide (8.5 g) is heated at reflux for 8 hours and allowed to cool. The crystallized product is collected by filtration, washed with water, and dried in air. After recrystallization from toluene, the product weighed 19.4 g (61.8% of the theoretical yield). Mass spectroscopy analysis indicates the product is the expected 4,4'-[(2-hydroxy-1,4-butanediyl)bis(oxy)]bis[benzaldehyde]. The bis-methine compound is reacted with ethyl cyanoacetate and the resulting product is recovered according to the procedure described in Example 37. Mass spectroscopy analysis is consistent with the structure:

EXAMPLE 43

Vanillin (30.4 g, 0.20 m) is dissolved in water (150 mL), containing sodium hydroxide (8.5 g). 1,4-Dibromo-2-butene (21.4 g, 0.1 m) is added and the reaction mixture heated at reflux for 6 hours. After the reaction mixture is cooled, the product is collected by filtration, washed with water, dried in air, and finally recrystallized from toluene (200 mL). The yield is 18.8 g (52.8% of the theoretical yield) of 4,4'-[2-butene-1,4-diylbis(oxy)]bis[3-methoxybenzaldehyde] as indicated by mass spectroscopy analysis. A mixture of 4,4'-[2-butene-1,4-diylbis(oxy)]bis[3-methoxybenzaldehyde] (3.56 g, 0.01 m), ethyl cyanoacetate (2.26 g, 0.02 m), ethanol (90 mL), and piperidine (10 drops) is heated at reflux for 4 hours. The reaction mixture is cooled and the product is collected by filtration, washed with ethanol, and dried in air (yield—4.3 g). Mass spectrum analysis supports the following structure:

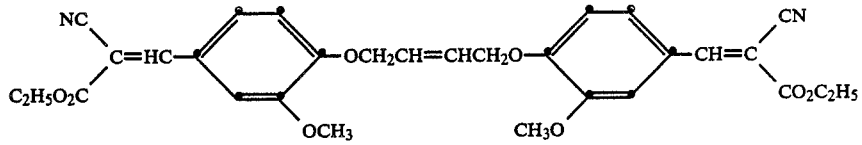

In methylene chloride, the product has an absorption maximum at 316 nm.

EXAMPLE 44 p-Hydroxybenzaldehyde (24.4 g, 0.20 m) is reacted with 1,4-dichloro-2-butyne (12.3 g, 0.10 m) by the same general procedure used in the previous example to yield 23 g (78.2% of the theoretical yield) of product after collecting by filtration, washing with water, and drying in air. Mass spectrum analysis indicates the product is 4,4'-[2-butyne-1,4-diylbis(oxy)]bis[benzaldehyde]. A mixture of 4,4'-[2-butyne-1,4-diylbis(oxy)]bis[benzaldehyde] (2.94 g, 0.01 m), ethyl cyanoacetate (2.26 g, 0.02 m), N,N-dimethylformamide (50 mL), and piperidine (10 drops) is heated at 85°-90° C. for 4 hours. The product is precipitated by the addition of water (20 mL), collected by filtration, washed with water, and dried in air (yield—3.6 g). Mass spectroscopy analysis supports the following structure:

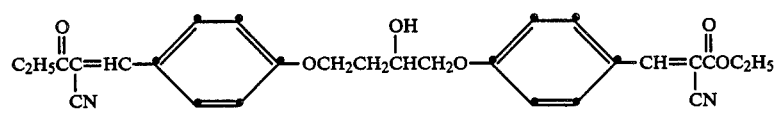

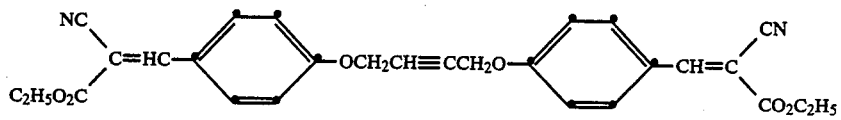

An absorption maximum (λmax) is observed at 330 nm in methylene chloride.

EXAMPLE 45

Vanillin (30.4 g, 0.2 m) is reacted with 2,3-dibromopropanol (21.8 g, 0.1 mol) according to the procedure employed in Example 41 to obtain 25.86 g of 4,4'-[[1-(hydroxymethyl)-1,2-ethanediyl]bis(oxy)]bis[3-methoxybenzaldehyde]. This intermediate (3.60 g, 0.01 m) is reacted with ethyl cyanoacetate as described in Example 41 to yield 4.3 g of product which mas spectroscopy indicated had the structure:

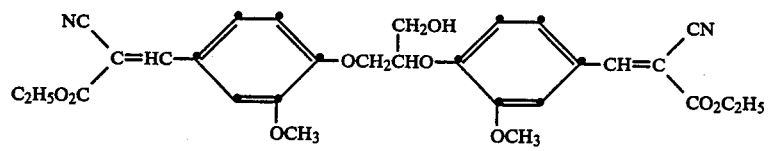

When dissolved in methylene chloride, the product has an absorption maximum (λmax) at 361 nm.

Table II describes additional poly-methine compounds which may be used in the preparation of the novel polymer compositions. These compounds may be prepared according to the procedures described in the preceding examples and conform to the formula:

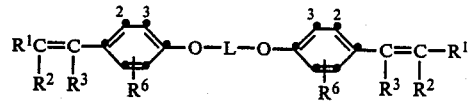

TABLE II

| Ex. | $R^1$ | $R^2$ | $R^3$ | $R^6$ | L |
|---|---|---|---|---|---|
| 46 | —CN | —COOC$_2$H$_5$ | —CH$_3$ | H | —CH$_2$CH(OH)CH$_2$— |
| 47 | —CN | —CN | —C$_6$H$_5$ | H | —CH$_2$CH(OH)CH$_2$— |
| 48 | —CN | —SO$_2$C$_6$H$_5$ | —C$_6$H$_{11}$ | H | —CH$_2$CH(OH)CH$_2$— |
| 49 | —CN | —COOCH$_3$ | H | 3-CH$_3$ | —CH$_2$CH(OH)CH$_2$— |
| 50 | —CN | —COOCH$_2$CH$_2$OH | H | 2-CH$_3$ | —CH$_2$CH(OH)CH$_2$— |
| 51 | —CN | —COOC$_6$H$_5$ | H | 2-Cl | —CH$_2$CH(OH)CH$_2$— |
| 52 | —CN | —CONH$_2$ | H | 2,5-di-CH$_3$ | —CH$_2$CH(OH)CH$_2$— |
| 53 | —CN | —COOC$_6$H$_{11}$ | H | 2,6-di-CH$_3$ | —CH$_2$CH(OH)CH$_2$— |
| 54 | —CN | —COOCH(CH$_3$)$_2$ | H | 2-Br | —CH$_2$CH$_2$CH(OH)CH$_2$— |
| 55 | —CN | —COOCH$_2$CH$_2$OH | H | 3-Cl | —CH$_2$CH$_2$CH(OH)CH$_2$— |
| 56 | —CN | —COOC$_2$H$_5$ | H | H | —CH$_2$CH$_2$CH(OH)CH$_2$— |
| 57 | —CN | —COOCH$_3$ | H | 3-OCH$_3$ | —CH$_2$CH$_2$CH(OH)CH$_2$— |
| 58 | —CN | —CN | H | H | —CH$_2$CH$_2$CH(OH)CH$_2$— |
| 59 | —CN | —COOH | H | H | —CH$_2$CH(OH)CH$_2$— |
| 60 | —CN | —SO$_2$CH$_3$ | H | H | —CH$_2$CH(OH)CH$_2$— |
| 61 | —CN | —C$_6$H$_4$—4-COOCH$_3$ | H | H | —CH$_2$CH(OH)CH$_2$— |
| 62 | —CN | —C=N—1,2-(4COOH)C$_6$H$_3$O | H | H | —CH$_2$CH(OH)CH$_2$— |
| 63 | —CN | —C=N—1,2-C$_6$H$_4$S | H | H | —CH$_2$CH(OH)CH$_2$— |
| 64 | —CN | —C=N—1,2-C$_6$H$_4$NH | H | H | —CH$_2$CH(OH)CH$_2$— |
| 65 | —CN | —C=N—1,2-C$_6$H$_4$C(O)NH | H | H | —CH$_2$CH(OH)CH$_2$— |
| 66 | —CN | —C=N—1,2-C$_6$H$_4$C(O)NCH$_3$ | H | H | —CH$_2$CH(OH)CH$_2$— |
| 67 | —COOC$_2$H$_5$ | —COOC$_2$H$_5$ | H | 3-OCH$_3$ | —CH$_2$CH(OH)CH$_2$— |
| 68 | —SO$_2$C$_6$H$_5$ | —SO$_2$C$_6$H$_5$ | H | 3-OCH$_3$ | —CH$_2$CH(OH)CH$_2$— |
| 69 | —COOC$_2$H$_5$ | —C=N—1,2-(3-Cl)C$_6$H$_3$O | H | 3-OC$_2$H$_5$ | —CH$_2$CH(OH)CH$_2$— |
| 70 | —CN | —CN | H | 3-OCH$_2$CH$_2$OH | —CH$_2$CH(OH)CH$_2$— |
| 71 | —CN | —COC$_6$H$_5$ | H | 3-OC$_6$H$_5$ | —CH$_2$CH(OH)CH$_2$— |
| 72 | —CN | —COC(CH$_3$)$_3$ | H | 3-OCH$_3$ | —CH$_2$CH(OH)CH$_2$— |

TABLE II-continued

| Ex. | R¹ | R² | R³ | R⁶ | L |
|---|---|---|---|---|---|
| 73 | —CN | —C=NN=C(C₆H₅)O (ring) | H | 3-OCH₃ | —CH₂CH(OH)CH₂— |
| 74 | —CN | —C=NN=C(CH₃)S (ring) | H | 3-OCH₃ | —CH₂CH(OH)CH₂— |
| 75 | —CN | —C=CHN=CHCH=CH (ring) | H | 3-OCH₃ | —CH₂CH(OH)CH₂— |
| 76 | —CN | —C=CHCH=CHS (ring) | H | 3-OCH₃ | —CH₂CH(OH)CH₂— |
| 77 | —CN | —C=CHCH=CHO (ring) | H | 3-OCH₃ | —CH₂CH(OH)CH₂— |
| 78 | —CN | —C=CHCH=CHNH (ring) | H | 3-OCH₃ | —CH₂CH(OH)CH₂— |
| 79 | —CN | —C=NCH=CHCH=N (ring) | H | 3-OCH₃ | —CH₂CH(OH)CH₂— |
| 80 | —CN | —SO₂(CH₂)₃OH | H | 3-OCH₃ | —CH₂CH(OH)CH₂— |
| 81 | —CN | —COC₆H₄—4-COOCH₃ | H | 3-OCH₃ | —CH₂CH(OH)CH₂— |
| 82 | —COOC₂H₅ | —SO₂C₆H₅ | H | 3-OCH₃ | —CH₂CH(OH)CH₂— |
| 83 | —COOC₂H₅ | —C=N—1,2-C₆H₄NH (ring) | H | 3-OCH₃ | —CH₂CH(OH)CH₂— |
| 84 | —COOC₂H₅ | —C=N—1,2-C₆H₄S (ring) | H | 3-OCH₃ | —CH₂CH(OH)CH₂— |
| 85 | —CN | —CONHCH₃ | H | 3-OCH₃ | —CH₂CH(OH)CH₂— |
| 86 | —CN | —CON(C₂H₅)₂ | H | 3-OCH₃ | —CH₂CH(OH)CH₂— |
| 87 | —CN | —COOC₂H₅ | H | 3-OCH₃ | —CH₂CH(OOCCH₃)CH₂— |
| 88 | —CN | —CONHC₆H₅ | H | 3-OCH₃ | —CH₂CH(OOCC₂H₅)CH₂— |
| 89 | —CN | —CONHC₆H₄—4-CH₃ | H | 3-OCH₃ | —CH₂CH(OOCOC₂H₅)CH₂— |
| 90 | —CN | —CONHC₆H₄—3-CH₃ | H | 3-OCH₃ | —CH₂CH(OOCC₆H₅)CH₂— |
| 91 | —CN | —CONHC₆H₄—2-OCH₃ | H | 3-OCH₃ | —CH₂CH(OOCNHC₆H₅)CH₂— |
| 92 | —CN | —COOCH₂CH₂Cl | H | 3-OCH₃ | —CH₂CH(OOCOC₆H₅)CH₂— |
| 93 | —CN | —COOCH₂C₆H₁₀—4-CH₂OH | H | 3-OCH₃ | —CH₂CH(OOCNHCH₂COOC₂H₅)CH₂— |
| 94 | —CN | —COOC₆H₁₁ | H | 3-OCH₃ | —CH₂CH(OOCC=CHCH=CHO (ring))CH₂— |
| 95 | —CN | —COOCH₂C₆H₅ | H | 3-OCH₃ | —CH₂CH(OOCC₆H₁₁)CH₂— |
| 96 | —CN | —COOCH₂CH₂OC₆H₅ | H | 3-OCH₃ | —CH₂CH(OOCCH₂CN)CH₂— |
| 97 | —CN | —CONHCH₂CH₂OH | H | H | —CH₂CH₂CH(OH)CH₂CH₂— |
| 98 | —CN | —CONHC₆H₄—4-OCH₃ | H | H | —CH₂CH(OH)— |
| 99 | —CN | —CN | H | H | —CH₂C(CH₂OH)₂CH₂— |
| 100 | —CN | —COOCH₃ | H | H | —CH₂C(CH₃)(CH₂OH)CH₂— |
| 101 | —CN | —SO₂CH₃ | H | H | —CH₂C(CH₂OOCCH₃)₂CH₂— |
| 102 | —CN | —COOC₂H₅ | H | H | —CH₂CH(Cl)CH₂— |
| 103 | —COOC₂H₅ | —COC₆H₅ | H | H | —CH₂CH(CN)CH₂— |
| 104 | —CN | —CN | H | H | —CH₂CH(COOCH₃)CH₂— |
| 105 | —CN | —SO₂C₆H₄—4-Cl | H | H | —CH₂CH(COOH)CH₂— |
| 106 | —CN | —CN | H | H | —CH₂CH(OC₆H₄—4-COOCH₃)CH₂— |
| 107 | —CN | —COOCH₃ | H | H | —CH₂CH(SCH₂CH₂OH)CH₂— |
| 108 | —CN | —CN | H | H | —CH₂CH(OC₆H₃—3,5-di-COOCH₃)CH₂— |
| 109 | —CN | —CN | H | H | —CH₂(SC₆H₄—2-COOH)CH₂— |
| 110 | —CN | —CN | H | H | —CH₂(OC₆H₄—4-COCl)CH₂— |
| 111 | —CN | —COOC₆H₅ | H | H | —CH₂CH(COOC₆H₅)CH₂— |
| 112 | —CN | —COOCH₃ | H | H | —CH₂CH(COOCH₂CH=CH₂)CH₂— |
| 113 | —CN | —COOCH₃ | H | H | —CH₂CH(COOC₆H₁₁)CH₂— |
| 114 | —CN | —COOCH₃ | H | H | —CH₂CH[OOCH(C₂H₅)₂]CH₂— |
| 115 | —CN | —COOCH(CH₃)₂ | H | H | —CH₂CH(NH₂)CH₂— |
| 116 | —CN | —CONHCH₂C₆H₁₁—4-CH₂OH | H | H | —CH₂CH[SO₂(CH₂)₃CH₃]CH₂— |
| 117 | —CN | —COOCH₂CH(OH)CH₂OH | H | H | —CH₂CH(SO₂C₆H₅)CH₂— |
| 118 | —CN | —COOCH₃ | H | H | —CH₂CH(SO₂CH₂CH₂OH)CH₂— |
| 119 | —CN | —CN | H | H | —CH₂CHNHSO₂C₆H₃—3,5-di-COOCH₃ with CH₂— branch |

TABLE II-continued

| Ex. | $R^1$ | $R^2$ | $R^3$ | $R^6$ | L |
|---|---|---|---|---|---|
| 120 | —CN | —COOCH$_3$ | H | H | —CH$_2$CH(CH$_2$—)NHCOC$_6$H$_4$—4-COOCH$_3$ |
| 121 | —CN | —COOCH$_2$CH=CH$_2$ | H | H | —CH$_2$CH(OC$_6$H$_5$)CH$_2$— |
| 122 | —CN | —COOCH$_3$ | H | H | —CH$_2$CH(CH$_2$—)OC$_6$H$_4$—4-CH=C(CN)COOCH$_3$ |
| 123 | —CN | —COOCH$_3$ | H | H | —CH$_2$C(CH$_2$—)(CH$_2$OC$_6$H$_4$—4-CH=C(CN)COOCH$_3$)CH$_2$OC$_6$H$_4$—4-CH=C(CN)COOCH$_3$ |
| 124 | —CN | —COOCH$_3$ | H | 3-OCH$_3$ | —CH$_2$CH=CHCH$_2$— |
| 125 | —CN | —CONHCH$_2$CH$_2$OH | H | 3-OCH$_3$ | —CH=CHCH$_2$— |
| 126 | —CN | —COOC$_2$H$_5$ | H | 3-OCH$_3$ | —CH$_2$C≡CCH$_2$— |
| 127 | —CN | —COOCH$_3$ | H | H | —CH(COOH)CH(COOH)— |
| 128 | —CN | —CN | H | H | —CH$_2$C(HOOC)=C(COOH)CH$_2$— |
| 129 | —CN | —COOCH$_3$ | H | H | —CH$_2$CH(COOCH$_3$)— |
| 130 | —CN | —CN | H | H | —CH$_2$CH(OCH$_2$C$_6$H$_4$—4-COOCH$_3$)CH$_2$— |
| 131 | —CN | —COOC$_6$H$_{11}$ | H | H | —CH$_2$CH(CH$_2$—)NHSO$_2$CH$_2$COOC$_2$H$_5$ |
| 132 | —CN | —COOCH$_2$C$_6$H$_{11}$ | H | H | —CH$_2$CH(CH$_2$—)N(CH$_3$)SO$_2$C$_6$H$_4$—3-COOCH$_3$ |
| 133 | —CN | —COONHC$_6$H$_{10}$—4OH | H | H | —CH$_2$CH(CH$_2$—)N(C$_6$H$_5$)SO$_2$C$_6$H$_4$—3-COOCH$_3$ |
| 134 | —CN | —COOCH$_3$ | H | H | —CH$_2$CH(CH$_2$—)N(CH$_3$)SO$_2$CH$_3$ |
| 135 | —CN | —COOC$_2$H$_5$ | H | H | —CH$_2$CH(CH$_2$—)N(SO$_2$CH$_3$)C$_6$H$_4$—3-COOC$_2$H$_5$ |
| 136 | —CN | —COOCH$_3$ | H | H | —CH$_2$CH(CH$_2$—)SO$_2$C$_6$H$_5$ |
| 137 | —CN | —COOCH$_3$ | H | H | —C≡CCH$_2$— |
| 138 | —CN | —CN | H | 3-OCH$_3$ | —CH$_2$CH(OH)CH(OH)CH$_2$— |
| 139 | —CN | —CN | H | 3-OCH$_3$ | —CH$_2$CH(OOCCH$_3$)CH(OOCCH$_3$)CH$_2$— |
| 140 | —CN | —COOCH$_3$ | H | 3-OCH$_3$ | —CH$_2$CH(OH)CH(OH)CH$_2$— |
| 141 | —CN | —COOCH$_3$ | H | H | —CH$_2$N(C(O)NCH$_2$CH$_2$)CH$_2$— |
| 142 | —CN | —COOC$_2$H$_5$ | H | H | —C=NC=NC(OCH$_3$)=N— |
| 143 | —CN | —COOC$_2$H$_5$ | H | 3-OH | —CH$_2$CH(OOCCH$_3$)CH$_2$— |

EXAMPLE 144

The following materials are placed in a 500-mL three-necked, round-bottom flask:

97 g (0.5 mol) dimethyl terephthalate
62 g (1.0 mol) ethylene glycol
0.00192 g Ti from a n-butanol solution of acetyl-triisopropyl titanate
0.0053 g Mn from an ethylene glycol solution of manganese acetate
0.0216 g Sb from an ethylene glycol solution of antimony acetate
0.0072 g Co from an ethylene glycol solution of cobaltous acetate The flask is equipped with a nitrogen inlet, stirrer, vacuum outlet, and condensing flask. The flask and contents are heated at 200° C. in a Belmont metal bath for 60 minutes and at 210° C. for 75 minutes with a nitrogen sweep over the reaction mixture. Then 1.57 mL of an ethylene glycol slurry of a mixed phosphorus ester composition (Zonyl A) which contains 0.012 g phosphorus is added. The temperature of the bath is increased to 230° C. At 230° C. dimethyl 3,3'-[1,2-ethanediyl-bis(oxy-1,4-phenylene)]bis[2-cyano-2-propenote] (0.0384 g) prepared in Example 1 is added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 minutes. The metal bath temperature is increased to 270° C. At 270° C. the pressure is reduced slowly to 100 mm Hg. The flask and contents are heated at 270° C. under a pressure of 100 mm Hg for 30 minutes. The metal batch temperature is increased to 285° C. and the pressure is reduced slowly to 4.5 mm Hg. The flask and contents are heated at 285° C. under pressur of 4.5 mm Hg for 25 minutes. Then the pressure is reduced to 0.25 mm Hg and polycondensation is continued for 40 minutes. The flask is removed from the metal bath and is allowed to cool in a nitrogen atmosphere while the polymer crystallizes. The resulting polymer has an inherent viscosity of 0.52 measured in a 60/40 ratio by weight of phenol/tetrachloroethane at a concentration of 0.5 g per 100 mL. An amorphous 13 mil thick film molded from this polymer to simulate the sidewall of a container transmits less than 10% light from 250 to 370 nm where a 13 mil film prepared from a like polyester without the copolymerized absorber transmits less than 10% light from 250 to only 320 nm.

EXAMPLE 145

The procedure described in Example 144 is repeated using 0.0384 g (440 ppm) of dimethyl 3,3'[1,3-propanediyl-bis(oxy-1,4-phenylene)]bis[2-cyano-2-propenoate] of Example 15 instead of the poly-methine compound used in Example 144. The resulting polymer is white and has an inherent viscosity of 0.53. An amorphous 13 mil thick film molded from this polymer transmits less than 10% light from 250 to 370 nm whereas a 13 mil film prepared from a like polyester without the copolymerized absorber transmits less than 10% light from 250 to only 320 nm.

EXAMPLE 146

The procedure described in Example 144 is repeated using 0.0384 g (400 ppm) of 3,3'-[(2-hydroxy-1,3-propanediyl)bis(oxy)bis(3-methoxy-4,1-phenylene)]-bis[2-(methylsulfonyl)-2-propenenitrile] obtained in Example 38 instead of the poly-methine compound used in Example 144. Resulting polymer has an inherent viscosity of 0.55 measured in a 60/40 ratio by weight of phenol/tetrachloroethane at a concentration of 0.5 g per 100 mL. An amorphous 15-mil thick film molded from this polymer shows a strong absorption peak with a maximum at 359 nm.

EXAMPLE 147

Example 144 is repeated using 0.0384 of diethyl 3,3'-[(2-hydroxy-1,3-propanediyl)bis(oxy)bis(4,1-phenylene)]bis[2-cyano-2-propenoate] from Example 40 instead of the poly-methine compound used in Example 144. The resulting polymer has an inherent viscosity of 0.56 measured in a 60/40 ratio by weight of phenol/tetrachloroethane at a concentration of 0.5 g per 100 mL. An amorphous 14-mil thick film molded from this polymer to simulate the sidewall of a container transmits less than 10% light from 250 to 366 nm where a 14-mil film prepared from a like polyester without the copolymerized absorber transmits greater than 10% light at all wavelengths above 320 nm.

EXAMPLE 148

Example 144 is repeated using 0.0384 of diethyl 3,3'-[(2-hydroxy-1,3-propanediyl)bis(oxy)bis(3-methoxy-4,1-phenylene)]bis[2-cyano-2-propenoate] prepared in accordance with Example 37 instead of the polymethine compound used in Example 144. The resulting polymer has an inherent viscosity of 0.56 measured in a 60/40 ratio by weight of phenol/tetrachloroethane at a concentration of 0.5 g per 100 mL. An amorphous 15-mil thick film molded from this polymer shows a strong absorption peak with a maximum at 366 nm.

The inherent viscosities (I.V.) of the copolyesters described herein are determined according to ASTM D2857-70 procedure in a Wagner Viscometer of Lab Glass Inc. of Vineland, N.J., having a ½ mL capillary bulb, using a polymer concentration of 0.5%, by weight, in 60/40, by weight, phenol/tetrachloroethane solvent. The procedure comprises heating the polymer/solvent system at 120° C. for 15 minutes to enhance dissolution of the polymer, cooling the solution to 25° C. and measuring the time of flow at 25° C. The I.V. is calculated from the equation:

$$\{\eta\}_{0.05\%}^{25°\ C.} = \frac{\ln \frac{t_s}{t_o}}{C}$$

where:
$\{\eta\}$ = Inherent viscosity at 25° C. at a polymer concentration of 0.5 g/100 mL of solvent;
ln = Natural logarithm;
$t_s$ = Sample flow time;
$t_o$ = Solvent-blank flow time; and
C = Concentration of polymer in grams per 100 mL of solvent = 0.50

The nonextractabilities of the methine residues described herein are determined as follows:

All extractions are done in glass containers with distilled solvents under the time and temperature conditions described below. The sample form is ½ inch × 2½ inch segments cut from the cylindrical side wall portion of 2-liter bottles. All samples are washed with cold solvent to remove surface contaminants and are exposed using 200 mL solvent 100 in.² surface area (2 mL/in.²).

Solvent blanks are run under the same extraction conditions without polymer. In most cases samples were extracted, spiked, with a known amount of additive as a control, and analyzed in duplicates. The solvents employed and the extraction conditions for each solvent are:

1. Water. The samples at room temperature are added to solvent and heated at 250° F. for 2 hours. Half of the samples are then analyzed and the remainder are placed in a 120° F. oven for 30 days.

2. 50% Ethanol/Water. The samples at room temperature are added to the solvent at room temperature, placed in an oven at 120° F. and analyzed after 24 hours. Another set of samples is aged for 30 days at 120° F. and then analyzed.

3. Heptane. The samples at room temperature are added to solvent at room temperature and heated at 150° F. for 2 hours. Part of the samples are cooled to room temperature and analyzed spectrophotometrically and the remainder are allowed to age at 120° F. for 30 days before analysis.

Any suitable analytical technique and apparatus may be employed to determine the amount of methine residue extracted from the polymer.

The invention has been described in detail with particular reference to preferred embodiments thereof, but it will be understood that variations and modifications can be effected within the spirit and scope of the invention.

We claim:

1. A composition comprising molding or fiber grade condensation polymer having copolymerized therein or reacted therewith the residue of a poly-methine compound or mixture of poly-methine compounds of the formula:

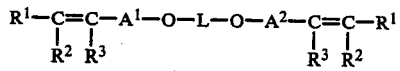

wherein
each R¹ is independently selected from cyano, carboxy alkenyloxycarbonyl or an unsubstituted or substituted alkoxycarbonyl, cycloalkoxycarbonyl or aryloxycarbonyl radical;
each R² is independently selected from one of the groups specified for R¹ or an unsubstituted or substituted aryl, carbamoyl, alkanoyl, cycloalkanoyl, aroyl, alkylsulfonyl, cycloalkylsulfonyl, arylsulfonyl or aromatic, heterocyclic radical;
each R³ is independently selected from hydrogen or an unsubstituted or substituted alkyl, cycloalkyl or aryl radical;
A¹ and A² each is an unsubstituted or substituted 1,4-phenylene radical; and
L is organic linking group bonded by non-oxo carbon atoms to the oxygen atoms adjacent to L; provided the poly-methine compound bears at least one substituent that is reactive with one of the monomers from which the condensation polymer is derived, said polymethine residue absorbing radiation in the range of about 250 nm to 390 nm and being nonextractable from said polymer and stable under polymer processing conditions.

2. A composition according to claim 1 wherein the polymer is a linear polyester having copolymerized therein at total of from about 200 to 800 ppm or the residue of the poly-methine compound or the mixture of poly-methine compounds.

3. A composition according to claim 1 wherein the polymer is a linear polyester having copolymerized therein a total of from about 50 to 1,500 ppm of a poly-methine compound or mixture of poly-methine compounds of formula:

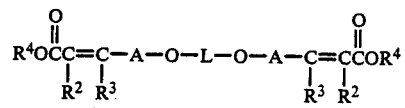

wherein
each R² is cyano, aryl, alkanoyl, aromatic heterocyclic, alkylsulfonyl, arylsulfonyl, aroyl, carbamoyl or carbamoyl substituted with aryl, alkyl or cycloalkyl;
each R³ is hydrogen, alkyl, aryl or cycloalkyl;
each R⁴ is hydrogen, alkyl, cycloalkyl, or aryl;
A is 1,4-phenylene; and
L is alkylene, alkylene—O—alkylene, alkylene—SO₂—alkylene, alkylene—S alkylene,

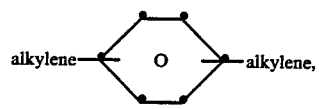

alkylene—O—alkylene—O—alkylene,

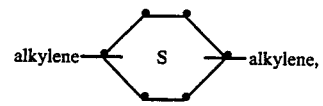

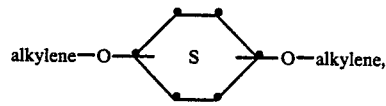

$$\text{alkylene}-\overset{SO_2-alkyl}{\underset{|}{N}}-\text{alkylene}, \text{alkylene}-\overset{CO-alkyl}{\underset{|}{N}}-\text{alkylene},$$

$$\text{alkylene}-\overset{CO-aryl}{\underset{|}{N}}-\text{alkylene}, \text{alkylene}-\overset{SO_2-aryl}{\underset{|}{N}}-\text{alkylene},$$

$$\text{alkylene}-\overset{aryl}{\underset{|}{N}}-\text{alkylene}, \text{alkylene}-\overset{\overset{NH-aryl}{|}}{\underset{|}{\underset{N}{C=O}}}-\text{alkylene},$$

$$\text{alkylene}-\overset{\overset{NH-aryl}{|}}{\underset{|}{\underset{N}{C=O}}}-\text{alkylene}, \text{alkylene}-\overset{alkyl}{\underset{|}{N}}-\text{alkylene},$$

$$\text{alkylene}-\overset{\overset{NH-cycloalkyl}{|}}{\underset{|}{\underset{N}{C=O}}}-\text{alkylene},$$

arylene, or cyclohexylene; wherein each alkyl, alkylene, aryl, arylene, cycloalkyl or cycloalkylene moiety or portion of a group or radical may be substituted where appropriate with 1–3 of hydroxyl, acyloxy, alkyl, cyano, alkoxycarbonyl, halogen, alkoxy, aryl, aryloxy, or cycloalkyl; wherein in all of the above definitions the alkyl or alkylene moieties or portions of the various groups contain from 1–8 carbons, straight or branched chain, the aryl or arylene nuclei contain from 6–10 carbons, and the cycloalkyl or cycloalkylene nuclei contain from 5–6 carbons.

4. A composition according to claim 3 wherein the total amount of polymethine residue present is from about 200 to about 800 ppm.

5. A composition according to claim 3 wherein
$R^2$ is cyano;
$R^3$ is hydrogen;
$R^4$ is alkyl;
A is 1,4-phenylene; and
L is alkylene or alkylene-phenylene-alkylene.

6. A composition according to claim 3 wherein L is methylene, ethylene, 1,4-butanediyl, 2-methyl-1,3-propanediyl, oxy-bis-ethylene, sulfonyl-bis-ethylene, thio-bis-ethylene, 1,4-phenylene-bis-methylene, 1,4-cyclohexylene-bis-methylene, 1,4-cyclohexylene-bis-(oxyethylene), methylsulfonyl-bis-ethylene, phenylimino-bis-ethylene, acetyl-imino-bis-ethylene, phenylsulfonylimino-bis-ethylene, 1,4-phenylene, 1,3-phenylene, 1,2-phenylene, 1,4-cyclohexylene, 1,4-phenylene-bis-ethylene, oxy-bis-1,4-butanediyl or phenylcarbamoylimino-bis-ethylene.

7. A composition according to claim 3 wherein the poly-methine compound has the structure:

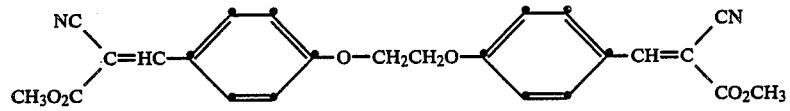

8. A composition according to claim 3 wherein the poly-methine compound has the structure:

9. A composition according to claim 3 wherein the poly-methine compound has the structure:

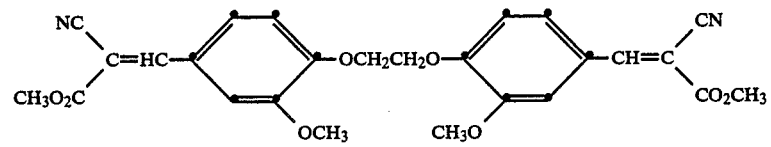

10. A composition according to claim 1 wherein the polymer is a linear polyester, the total amount of polymethine residue present is from about 50 to 1,500 ppm and L is alkenylene, alkynylene or alkylene substituted with hydroxy, carboxy, chlorocarbonyl, alkoxycarbonyl, cycoalkoxycarbonyl, aryloxycarbonyl, alkenyloxycarbonyl, carbamoyloxy, amino, alkylamino, alkanoyloxy, halogen, or a group having the formula:

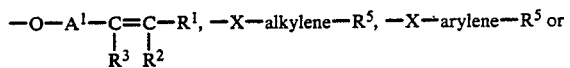

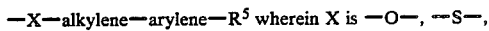 wherein X is —O—, —S—,

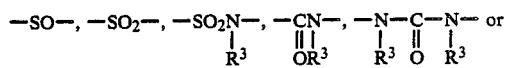

in which $R^1$, $R^2$, $R^3$, and $A^1$ are defined in claim 1 and $R^5$ is hydrogen, hydroxy, carboxy, chlorocarbonyl, alkoxycarbonyl, cycloalkoxycarbonyl, aryloxycarbonyl, alkenyloxycarbonyl, carbamoyloxy, amino, alkylamino, alkanoyloxy or halogen.

11. A composition according to claim 1 wherein the polymer is a linear polyester having copolymerized therein or reacted therewith a total of from about 50 to 1,500 ppm of the residue of a polymethine compound of the formula:

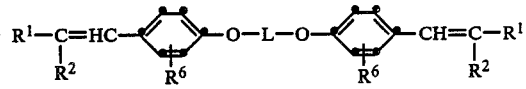

wherein
$R^1$ is alkoxycarbonyl, carboxy, or cyano;
$R^2$ is alkoxycarbonyl, carboxy, cyano or alkylsulfonyl;
$R^6$ is hydrogen, alkyl or alkoxy; and
L is alkylene substituted with hydroxy or alkanoyloxy.

12. A composition according to claim 11 wherein the poly-methine compound has the structure:

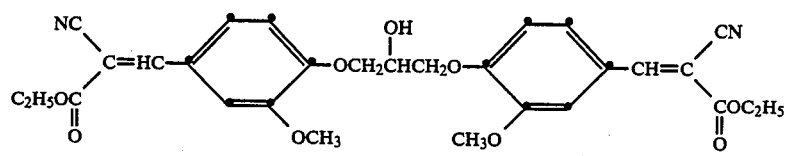

13. A composition according to claim 11 wherein the poly-methine compound has the structure:

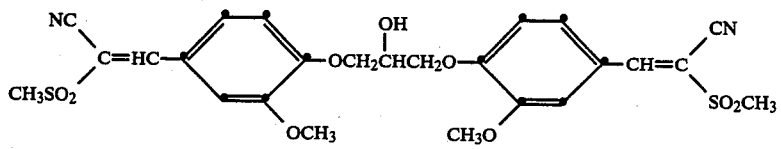

14. A composition according to claim 11 wherein the poly-methine compound has the structure:

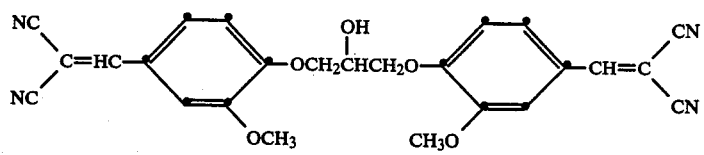

15. A composition according to claim 11 wherein the poly-methine compound has the structure:

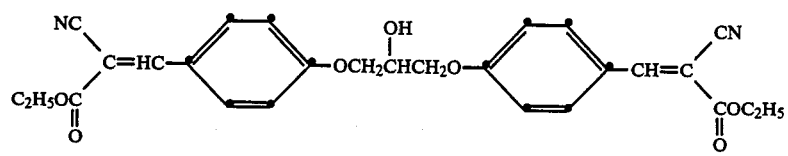

16. A composition according to claim 11 wherein the poly-methine compound has the structure:

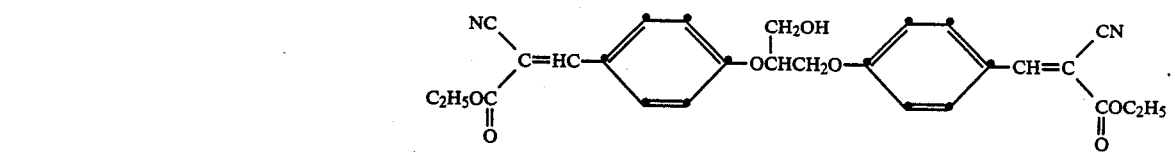

17. A composition according to claim 11 wherein the poly-methine compound has the structure:

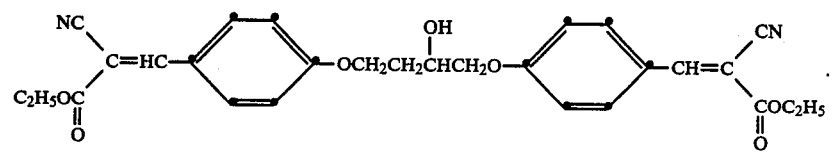

18. A composition according to claim 10 wherein the poly-methine compound has the structure:

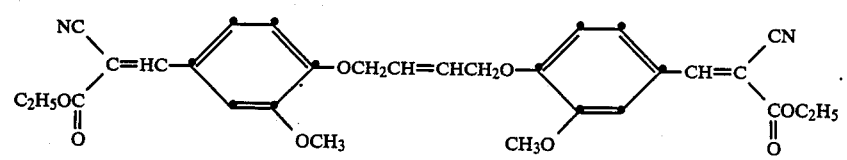

19. A composition according to claim 10 wherein the poly-methine compoundhas the structure:

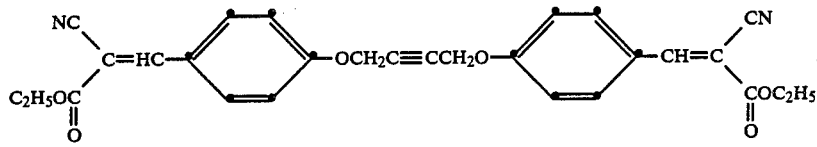

20. A composition according to claim 11 wherein the poly-methine compound has the structure:

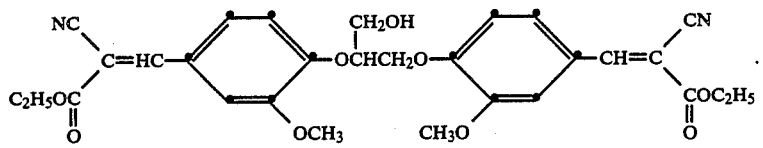

glycol, neopentyl glycol, 2,2,4-trimethyl-1,3-pentanediol, ethylene glycol or diethylene glycol.

21. The composition of any one of claim 1-7, 10 or 11 wherein the polyester acid moiety is comprised of at least about 50 mol % terephthalic acid residue, and the glycol moiety at least about 50 mol % ethylene glycol or 1,4-cyclohexane-dimethanol residue, and the polyester contains a total of from about 2 to about 1,500 ppm of one or a mixture of the bis-methine moieties.

22. The composition of any one of claims 1-7, 10 or 11 wherein the polyester is comprised of from about 75 to 100 mol % terephthalic acid residue and from about 75 to 100 mol % ethylene glycol residue.

23. The composition of claim 1 wherein the polymer is unsaturated polyester having an acid moiety comprised of fumaric or maleic acid or mixtures thereof and up to about 60 mol % of one or a mixture of o-phthalic, iso-phthalic, or terephthalic acids, and having a glycol moiety comprised of one or a mixture of propylene 24. The composition of claim 23 wherein the acid moiety is comprised of from about 75 to 100 mol % o-phthalic acid and maleic acid in a mole ratio of from about ½ to about 2/1, and the glycol moiety is comprised of from about 75 to 100 mol % propylene glycol.

25. The composition of claim 23 containing a curing amount of an ethylenically unsaturated monomer.

26. A formed article of the composition of any one of claims 1 through 5.

27. A formed article of the composition of claim 11.

28. A composition according to claim 1 wherein the polymer is a linear polyester having reacted therein a total of about 2.0 to 10.0 weight percent of the residue of a difunctional poly-methine compound or mixture of compounds of the formula set forth in claim 1.

* * * * *